United States Patent [19]
Rheinheimer et al.

[11] Patent Number: 5,895,765
[45] Date of Patent: Apr. 20, 1999

[54] METHOD FOR THE DETECTION OF AN ANALYTE BY IMMUNOCHROMATOGRAPHY

[75] Inventors: Gary W. Rheinheimer, Goshen; Meitak Teresa Yip, Elkhart, both of Ind.

[73] Assignee: Bayer Corporation, Elkhart, Ind.

[21] Appl. No.: 08/885,285

[22] Filed: Jun. 30, 1997

[51] Int. Cl.$^6$ .................................................. G01N 33/558
[52] U.S. Cl. .......................... 436/514; 435/7.1; 435/7.92; 435/7.93; 435/7.94; 435/7.95; 435/962; 435/970; 436/518; 436/525; 436/528; 436/530; 436/810; 436/825; 514/668; 510/421; 510/423; 510/429; 510/499; 510/506
[58] Field of Search .......................... 435/7.1, 7.92–7.95, 435/962, 970; 436/518, 514, 528, 525, 530, 810, 825; 510/421, 423, 429, 499, 506; 514/668

[56] References Cited

U.S. PATENT DOCUMENTS

| | | | |
|---|---|---|---|
| 4,847,209 | 7/1989 | Lewis et al. | 436/533 |
| 5,102,788 | 4/1992 | Cole | 435/7.9 |
| 5,120,643 | 6/1992 | Ching et al. | 435/7.92 |
| 5,393,668 | 2/1995 | Cinad et al. | 435/240.23 |
| 5,451,504 | 9/1995 | Fitzpatrick et al. | 435/7.2 |
| 5,459,080 | 10/1995 | Adamczyk et al. | 436/538 |
| 5,559,041 | 9/1996 | Kang et al. | 436/518 |
| 5,610,287 | 3/1997 | Nikiforov et al. | 536/24.3 |
| 5,622,871 | 4/1997 | May et al. | 436/514 |
| 5,639,626 | 6/1997 | Kiaei et al. | 435/7.92 |

FOREIGN PATENT DOCUMENTS

| | | | |
|---|---|---|---|
| 0 699 908 | 3/1996 | European Pat. Off. | 435/7.92 |
| 0 713 095 | 5/1996 | European Pat. Off. | 435/7.92 |

*Primary Examiner*—Carol A. Spiegel
*Attorney, Agent, or Firm*—Jerome L. Jeffers

[57] ABSTRACT

Disclosed is an improved method for the detection of an analyte in a fluid test sample using a strip of a negatively charged matrix material having a zone containing mobile, labeled binding partner for the analyte and a separate zone for capturing the labeled binding partner as it is carried through this zone by the fluid test sample. The improvement involves combining the fluid test sample with a polyalkoxylated amine surfactant to control non-specific binding of the labeled binding partner to the negatively charged matrix material.

12 Claims, 1 Drawing Sheet

METHOD FOR THE DETECTION OF AN ANALYTE BY IMMUNOCHROMATOGRAPHY

BACKGROUND OF THE INVENTION

There is a need for simple diagnostic tests for common diseases which can be carried out by untrained personnel. Such tests facilitate home or doctor's office testing as opposed to more complicated procedures which require that the analysis be carried out in an outside reference laboratory. A common format for these tests is the immunostrip format. Typically, this format involves a matrix of a material through which a fluid test sample can flow by capillarity. The matrix, typically in the form of a strip, contains an analyte specific antibody which bears a detectable label so that the presence and/or concentration of the analyte in the test fluid can be determined by detection of the signal emitted from the detectable label. A classical format for such a device, sometimes referred to as an immunochromatographic strip, is illustrated by FIG. 1. Referring to FIG. 1, strip 10, bears a labeled antibody specific for the analyte under investigation in zone 13 which binds with the analyte in the fluid test sample applied to the wicking zone 12 of the strip 10 and flows along the strip to form an immunocomplex which further migrates due to capillary action through the capture zone of the strip 14 and the optional detection zone 16. In the capture zone 14 there is immobilized the analyte or a derivative thereof which is immunoreactive with the labeled antibody and is able to capture labeled antibody which has not reacted with analyte in the fluid test sample. The signal from the labeled antibody captured in the capture zone is measured and related to the concentration of analyte in the test fluid in an inverse relationship since the greater the concentration of analyte in the test sample, the amount labeled antibody which is unbound and thereby free to specifically bind with analyte immobilized in the detection zone is diminished. Detection zone 16 is optional but can contain immobilized anti-mouse IgG to bind the analyte/labeled binding partner complex and thereby serve as a means for verifying that the test has been carried out correctly.

A problem with this sort of test device involves the tendency of labeled antibody and its conjugate to engage in non-specific binding (NSB) with the matrix material forming the strip. When such non-specific binding takes place, the labeled antibody binds to the matrix material before it reaches the capture zone and the assay fails because the movement of labeled antibody is either completely stopped or diminished such that the signals in the capture zone and detection zone are greatly reduced.

In order to correct this bias, the strip can be treated with a blocking solution such as 1% casein in phosphate buffered saline (PBS), washed with water and dried after deposition of the reagents onto the capture and collection zones. This blocking step, however, is problematic since there is required extensive development effort to optimize the blocked system.

In U.S. Pat. No. 5,451,507 there is described the preparation of a blocked nitrocellulose membrane for use as an immunochromatographic strip in which the nitrocellulose membrane is incubated in a solution of 1 mg/mL bovine IgG in sodium sulfate buffer for 30 minutes before being incubated with glutaraldehyde and bovine IgG. This reference also mentions the desirability in some instances of including from about 0.05 to 0.5 weight percent of a non-ionic detergent with the fluid test sample.

It would be desirable, and it is an object of the present invention to provide a means for reducing or eliminating non-specific binding of labeled specific binding partner in the capture and detection zones of the type of immunochromatographic strip under consideration.

SUMMARY OF THE INVENTION

Figure 1:
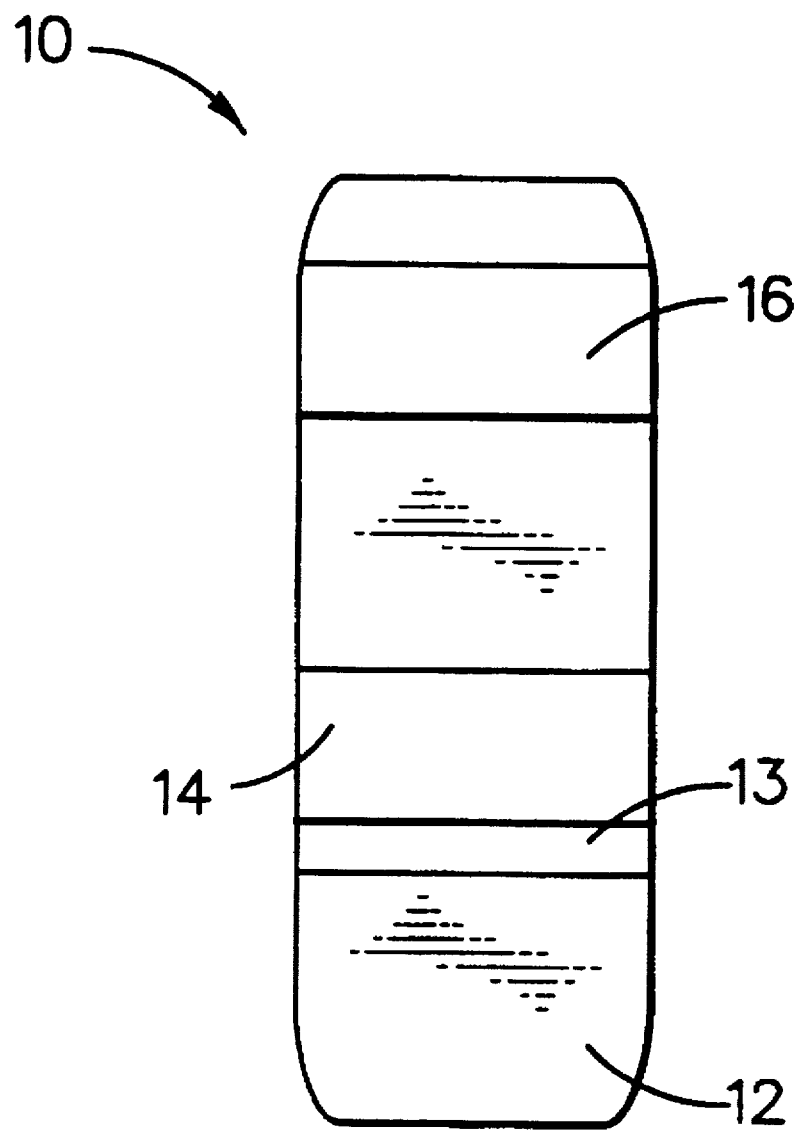
FIG. 1 represents an immunostrip suitable for use in the present invention.

The present invention involves a method for the determination of the concentration of an analyte in a fluid test sample which comprises the steps of:

a) providing a matrix through which the fluid test sample can flow by capillarity which matrix comprises a negatively charged polymeric material and has a first region containing mobile specific binding partner for the analyte which bears a detectable label and can react with the analyte to form an analyte/labeled binding partner complex and a second region which contains immobilized analyte or an immobilized binding partner which is specific for an epitope of the analyte different from that to which the labeled binding partner is specific;

b) combining the fluid test sample with a cationic surfactant which is a polyalkoxylated amine; and c) developing the matrix by the application of the fluid test sample suspected of containing the analyte and allowing the fluid to contact the mobile specific binding partner so that analyte present in the fluid test sample forms an analyte/labeled specific binding partner complex and leaves excess, unreacted labeled binding partner free to further react whereby the fluid test sample carries the analyte/labeled binding partner complex and unreacted labeled specific binding partner along the strip by capillarity to the second region containing the immobilized analyte in which region unreacted, labeled specific binding partner is bound to immobilized analyte in an inverse relationship to the concentration of the analyte in the fluid test sample or is bound to the immobilized specific binding partner in direct relationship to the concentration of analyte in the fluid test sample. The surfactant results in non-specific binding of the labeled specific binding partner to the test strip being reduced.

DESCRIPTION OF THE INVENTION

The present invention is practiced by first providing a test strip in the form of a matrix through which the test sample can flow by capillarity. Typically, the matrix will be in the form of a strip through which the test fluid flows horizontally, although the matrix could be set up in layers through which the test fluid could flow vertically from top to bottom or vice-versa. The following discussion focuses on the strip format.

The strip can be prepared from any negatively charged matrix material through which the test fluid and the analyte contained therein can flow by capillarity. Accordingly, suitable matrix materials include nitrocellulose, polysulfones and polycarboxylic acids. Nitrocellulose is a preferred material from which to fabricate the strip. These materials are related in that they bear a negative charge.

A particularly suitable immunochromatographic strip format for use in relation to the present invention is that format which is disclosed in U.S. Pat. No. 4,446,232 wherein there is described a device for the determination of the presence of antigens, which device comprises a strip of a matrix material having a first zone in which there are provided immobilized and enzyme linked antibodies specific to the analyte to be determined. The labeled antibodies can flow to a second zone when reacted with analyte introduced into the first zone along with the test fluid but will not so flow in the absence of analyte in the test fluid due to their being bound in the first zone by interaction with the immobilized analyte. The analyte is typically an antigen although the format can be designed to detect the presence of antibodies as analyte. An alternative to this format is that in which the detection zone contains an immobilized binding partner which is specific for an epitope of the analyte different from that to which the labeled binding partner is specific. This provides a means for capturing the labeled binding partner using the so-called sandwich format. In another modification, there is disposed in a separate region of the strip an immobilized binding partner for the conjugate such as anti-mouse IgG to thereby capture the complex formed between the labeled specific binding partner and the analyte. Thus, by immobilizing the conjugate in a discrete detection zone located downstream on the strip from the zone in which the labeled binding partner for the analyte is bound, there are provided two zones from which the physically detectable property of the detectable label can be measured to determine its intensity and hence the concentration of the detectable label in a particular region of the strip. By measuring the signal from the physically detectable property of the detectable label in the second zone containing the immobilized analyte or binding partner specific to a defined epitope of the analyte as the capture means and the physically detectable property of the label in the third zone, in which the immobilized antibody against the labeled binding partner is the capture means, and determining the ratio of these signals, the accuracy of the test for analyte concentration can be increased.

Regardless of the selection of the format for the assay, the accuracy of the final result can be skewed by non-specific binding (NSB) of the labeled binding partner to the matrix material and it is the goal of the present invention to reduce or eliminate this problem without the necessity of carrying out the extra step of applying a separate blocking layer to the negatively charged membrane. This is accomplished by combining the appropriate polyalkoxylated amine surfactant with the fluid test sample which can be accomplished by various methods such as by mixing the fluid test sample with the surfactant before contacting it with the strip. An alternative method is to treat the strip's wicking pad with the surfactant, so that it is rehydrated upon contact with the fluid test sample and flow with the test sample to the labeled binding partner zone (13 in FIG. 1), capture zone and detection zone. A third and preferred method is to combine the surfactant with the labeled binding partner and apply the combination to zone 13 thereby causing it to become part of the test strip whereby rehydration occurs upon contacting the strip with the fluid test sample resulting in the surfactant flowing with the labeled binding partner and labeled binding partner/analyte complex to the capture and detection zones. Any one of these methods provides the necessary dispersion of the surfactant in the test sample. Preferred surfactants are available under the tradename Tetronic®. The Tetronic surfactants are tetrafunctional block copolymers derived from the sequential addition of propylene oxide and ethylene oxide to ethylenediamine. The amine moiety in these surfactants provides the surfactants with slightly cationic properties and contributes to their thermal stability. The Tetronic surfactants have the poly-propoxy groups bonded directly to the amine nitrogens with the polyethoxy groups comprising the pendent portions of the surfactant molecule. This is in contrast to the less effective (for purposes of inhibiting non-specific binding) Tetronic® R surfactants which are produced by the sequential addition of ethylene oxide and propylene oxide to ethylenediamine resulting in a surfactant having the poly-ethoxy groups interspersed between the amine nitrogens and the poly-propoxide groups.

It has also been discovered that the labeled binding partner such as a gold sol labeled antibody (GSA) can be caused to more readily release from the first region of the strip, combine with the test sample and to flow along the strip to the capture and detection zones by the introduction of a saccharide into the assay. The saccharide, which may include but is not limited to trehalose, sucrose, fructose or maltose, is typically combined with the labeled binding partner in an amount of from 0.2% to 5% by weight per OD of the labeled binding partner.

Typically, the test fluid is urine although other body fluids, such as whole blood, plasma, serum, sweat or saliva can be tested. Many clinically significant analytes are present in urine and other body fluids and are determinable by means of the present invention. Among these analytes are deoxypyridinoline (DPD), human serum albumin, prostate specific antigen, drugs of abuse, TDM drugs, cancer markers, cardiac markers, hCG, strep A and Helicobacter pylori. The detectable label for the analyte may be any moiety which is detectable by reproducible means. Thus, the label can be an enzyme, a radio isotope, a chemilluminscent material or, preferably, a visible particulate label such as gold sol.

The method of practicing the invention is further illustrated by the following examples:

EXAMPLE I

A strip (2.54 cm×43.18 cm) of nitrocellulose membrane was used to prepare a test strip similar to that depicted in FIG. 1 except that the strip had three capture zones 14. Reagents were deposited onto the nitrocellulose membrane in the following manner: One band of anti-mouse IgG (1 mg/ml of PBS) was deposited onto the matrix at about 3 and 3.5 cm from the bottom in amounts of 2 µL and 1 µL respectively after which 3 bands of DPD-PEG conjugate (1 mg/mL of PBS) were deposited on the nitrocellulose membrane at about 0.5, 1 and 1.5 cm from the bottom at 2 µL/cm to provide three capture zones. The treated membrane was dried at 40° C. for about 17 minutes.

A gold sol-anti DPD antibody (GSA) suspension was prepared having the following composition: GSA (10 OD) in 2 mM borate at pH 9, 14.6% (1.46% per OD of GSA, OD is an optical density unit at 530 nm) trehalose, 0.5% bovine serum albumin (BSA) and 1.26% (0.126% per OD of GSA) Tetronic 1307 as surfactant. An aliquot of 3 µL of GSA suspension was pipetted onto a GSA pad (0.2"×0.2", Whatman glass fiber F075-07) and air dried. The nitrocellulose strip containing the capture zone and detection zone was assembled on a polystyrene backing using an acrylic based adhesive. The GSA pad was assembled adjacent to the nitrocellulose with a 0.04" overlap. The wicking pad (0.5"× 0.2", Whatman glass filter F075-07) was then assembled adjacent to the GSA pad with 0.04" overlap.

For testing, the strips were dipped into a test tube containing the test solution, i.e. urine containing a measured amount of DPD, for about 3 seconds, removed from the solution and placed on the specimen table of a CLINITEK® 50 reflectance meter which measured and recorded the % reflectance of each of the capture and detection bands. A linear dose response curve was obtained for seven concentrations of DPD ranging from 0 to 250 nM.

The experiment was repeated with other Tetronic and Tetronic R surfactants at various concentrations of the gold sol-anti DPD suspension. In each case the release of the GSA from the pad upon application of the test fluid was measured by the amount of GSA (red color) left on the GSA pad 3 minutes after the strip was dipped into the test solution. A "–" was used to indicate greater than 80% of GSA left on the pad. One "+" indicates poor release with greater than 50% GSA left on the pad and "++++" indicates good release with less than 10% GSA left on the pad. Two and three "+" ratings were given for intermediate release values. The non specific binding of the gold sol labeled anti DPD to the nitrocellulose strip was determined by the amount of GSA (red color), after release from the GSA pad, bound to the nitrocellulose in the areas where neither capture reagent nor detection reagent was applied such as the area between the GSA pad and the first capture band and the area between the capture zone and the detection zone. The GSA should not bind to these areas because they contain no capture or detection reagent to bind to the antibody. When no surfactant was used in the formulation, greater than 90% of the GSA was non-specifically bound in the area between the GSA pad and the first capture band. A rating system for non-specific binding was established in which "–" indicates greater than 80% of the GSA engaged in non-specific binding, one "+" indicated very strong non-specific binding with greater than 50% of the BSA bound in areas other than the capture and detection zones and "++++" indicates very little non-specific binding of less than 10%. Two and three "+" ratings were given for intermediate release values. The results of these experiments are tabulated in Table 1.

TABLE 1

| Class | Surfactants | Average Molecular weight | % | Released from GSA pad | NSB on nitrocellulose |
|---|---|---|---|---|---|
| Tetronic R | 70 R-2 | 3870 | 0.8 | + | ++ |
| | 150 R-1 | 8000 | 0.8 | ++ | ++ |
| Tetronic | 1301 | 6800 | 0.8 | +++ | ++++ |
| | 1501 | 7900 | 0.8 | +++ | ++++ |
| | 1107 | 15000 | 0.8 | ++++ | ++++ |
| | 1307 | 18000 | 0.14 | +++ | ++++ |
| | | | 0.2 | +++ | ++++ |
| | | | 0.7 | ++++ | ++++ |
| | | | 1.3 | ++++ | ++++ |
| | | | 5 | ++++ | ++++ |
| | 1508 | 30000 | | ++++ | ++++ |

The Tetronic surfactants used are produced by BASF. There are two classes of Tetronic surfactants; Tetronic and Tetronic R. The Tetronic surfactants are tetrafunctional block copolymers derived from the sequential addition of propylene oxide and ethylene diamine. The resulting polymeric surfactants carry the propylene group next to the amine group. The Tetronic R surfactants are tetrafunctional block copolymers derived from the sequential addition of ethylene oxide and propylene oxide to ethylenediamine resulting in polymeric surfactants which carry the ethylene group next to the amine group. Both of these classes of surfactant contain the amine functional group which provides a cationic property to the molecule. Since nitrocellulose and various other matrix materials are negatively charged, the positively charged surfactants tend to bind to the nitrocellulose surface thereby blocking the nonspecific binding of the gold sol-antibody conjugate. Based on the data presented in Table 1, the Tetronic surfactants are preferred over the Tetronic R surfactants both in terms of enhancement of GSA release and inhibition of nonspecific binding. Certain of the higher molecular weight Tetronics beginning at above 7900 are particularly preferred since, with only minor exceptions, they provide four "+" performance in both categories. As indicated by the data relating to Tetronic 1307, performance improves with increased concentration of the surfactant although the data suggest that concentrations above 0.7% are not necessary to achieve the desired results.

The desirable molecular weights for the Tetronic surfactants are greater than 5,000 and preferably greater than 10,000 with a molecular weight in the range of from 10,000 to 30,000 being particularly desirable. The concentration of the surfactant used is typically 0.5 to 10% and preferably 0.05% to 1% by weight per OD of the GSA when the surfactant is included in the GSA formulation. Each strip is typically prepared with 30 OD of the gold sol labeled antibody. When the surfactant is included in the strip, a loading of 15 μg to 1,000 μg per strip is usually sufficient. When the surfactant is added to the test sample, a concentration of 0.02% to 1.3% by weight is used.

Despite the successful experiments with the Tetronic cationic surfactants, other cationic surfactants which were tested in a similar manner did not prove to be as successful as the Tetronics. The results of these experiments are tabulated in Table 2 wherein a "–" indicated that lack of GSA release and non-specific binding were very severe.

TABLE 2

| Type | Compound | Conc, % | Released from GSA pad | NSB at NC |
|---|---|---|---|---|
| Cationic | Benzalkonium chloride | 0.6% | – | + |
| | Benzyldimethyltetradecyl-ammonium chloride | 0.8% | – | – |
| | Decamethonium bromide | 0.8% | – | – |
| | Benzyldimethylhexadecyl-ammonium chloride | 0.8% | – | – |
| | Dimethyldioctadecyl-ammonium bromide | 0.8% | – | – |
| | Methyltrioctylammonium chloride | 0.8% | – | – |
| | Benzyldimethyldodecyl-ammonium bromide | 0.8% | – | – |
| | Cetylpyridinium chloride | 0.8% | + | – |
| | Cetyldimethylethylammonium bromide | 0.8% | ++ | ++ |

EXAMPLE II

In order to demonstrate the advantage of combining the cationic surfactants useful in the present invention with a saccharide a study was carried out involving the following two formulations:

A: Gold sol antibody conjugate: 1.7 OD (@ 530 nm)
Trehalose: 2.5%
Tetronic 1107: 0.17%
BSA: 0.06%

B: Gold sol antibody conjugate: 1.7 OD (@ 530 nm)
Tetronic 1107: 0.17%
BSA: 0.06%

All percentages are based on weight, i.e. weight % of the component to weight of the GSA suspension. After drying the membrane, the gold sol antibody conjugate from formulation B became aggregated and its release and flow were found to be much worse than that of formulation A.

We claim:

1. A method for determining the presence or amount of an analyte in urine, which comprises:
   a) contacting the urine with a strip of nitrocellulose, said strip comprising
      (i) a wicking region for application of the urine,
      (ii) a region comprising a mobilizable, labeled antibody which specifically binds the analyte and a surfactant which is a tetrafunctional block copolymer derived from sequential addition of propylene oxide and ethylene oxide to ethylenediamine, said surfactant comprising poly-propoxy groups bonded directly to amine nitrogens with polyethyoxy groups, wherein the amine nitrogens with polyethyoxy group form pendent portions of the surfactant, said surfactant having a molecular weight of from 10,000 to 30,000 and wherein the surfactant is present in an amount which is effective to reduce non-specific binding of the labeled antibody to the nitrocellulose, and
      (iii) a capture zone in which there is immobilized a specific binding partner which specifically binds to the labeled antibody, thereby mobilizing the labeled antibody, forming a specific binding complex between the labeled antibody and any analyte in the contacted urine, and carrying the complex, contacted urine sample and unreacted labeled antibody through the nitrocellulose by capillary flow to the capture zone where unreacted labeled antibody specifically binds to the immobilized specific binding material in inverse relationship to the amount of the analyte in the contacted urine; and
   b) correlating the amount of unreacted labeled antibody bound in the capture zone to the amount of the analyte in the urine contacted with the strip.

2. The method of claim 1 wherein the analyte is deoxypyridinoline.

3. The method of claim 1 wherein the labeled antibody is labeled with gold sol.

4. A test strip for determination of an analyte in a urine test sample, which comprises;
   a matrix of nitrocellulose comprising
      (a) a first region comprising (i) a mobilizable specific binding partner for the analyte which binding partner is coupled to a detectable label and which reacts with a first epitope of the analyte to form an analyte/labeled specific binding partner complex together with (ii) a tetrafunctional block copolymer derived from sequential addition of propylene oxide and ethylene oxide to ethylenediamine, said surfactant comprising polypropoxy groups bonded directly to amine nitrogens with polyethoxy groups, wherein the amine nitrogens with polyethoxy groups form pendent portions of the surfactant and wherein the surfactant is in an amount effective to reduce non-specific binding of the labeled specific binding partner to the nitrocellulose; and
      (b) a second region comprising an immobilized analyte or an immobilized specific binding partner which specifically binds a second epitope of the analyte different from the first epitope.

5. The test strip of claim 4 further comprising (c) a third region comprising an immobilized means which specifically binds to the analyte/labeled specific binding partner complex downstream of the second region.

6. The strip of claim 4 wherein the labeled specific binding partner is a gold sol labeled antibody.

7. A method for determining the presence or amount of an analyte in a urine sample, comprising:
   a) providing a negatively charged matrix comprising nitrocellulose through which the urine sample can flow by capillarity, said matrix comprising (i) a first region comprising mobilizable, labeled specific binding partner for a first epitope of the analyte and (ii) a second region comprising either immobilized analyte or an immobilized specific binding partner which specifically binds a second epitope of the analyte different from the first epitope;
   b) combining the sample with a cationic surfactant which is a tetrafunctional block copolymer derived from sequential addition of propylene oxide and ethylene oxide to ethylenediamine, said surfactant comprising polypropoxy groups directly bonded to amine nitrogens with polyethoxy groups, wherein the amine nitrogens with polyethoxy groups form pendent portions of the surfactant and wherein the surfactant is in an amount effective to reduce non-specific binding of the labeled specific binding partner to the matrix;
   c) applying the combined sample to the matrix to contact and mobilize the labeled specific binding partner such that any analyte in the applied sample forms a specific binding complex with the labeled specific binding partner and carries said complex, unreacted applied sample, and unreacted labeled specific binding partner through the matrix by said capillary flow to the second region wherein either the unreacted labeled specific binding partner is specifically bound to the immobilized analyte in inverse relationship to the amount of the analyte in the applied sample or the complex is specifically bound to the immobilized specific binding partner in direct relationship to the amount of the analyte in the applied sample; and,
   d) correlating the amount of the unreacted labeled specific binding partner or the amount of the complex bound in the second region to the presence or amount of the analyte in the urine sample.

8. The method of claim 7 in which the flow is horizontal.

9. The method of claim 7 wherein the sample is combined with the surfactant before the combined sample is applied to the matrix.

10. The method of claim 7 wherein the surfactant is provided on the matrix in a dry form upstream of the first region and wherein the sample is contacted with the dried surfactant to provide the combined sample.

11. The method of claim 7 wherein the first region further comprises a saccharide in an amount sufficient to facilitate mobilization of the labeled specific binding partner therefrom.

12. The method of claim 7 wherein the labeled specific binding partner is a colloidal gold labeled antibody.

* * * * *